US006723119B2

(12) United States Patent
Pinchasik et al.

(10) Patent No.: US 6,723,119 B2
(45) Date of Patent: *Apr. 20, 2004

(54) LONGITUDINALLY FLEXIBLE STENT

(75) Inventors: Gregory Pinchasik, Herzlia (IL); Jacob Richter, Ramat Hasharon (IL)

(73) Assignee: Medinol Ltd., Tel Aviv (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/864,160

(22) Filed: May 25, 2001

(65) Prior Publication Data

US 2002/0007211 A1 Jan. 17, 2002

Related U.S. Application Data

(63) Continuation-in-part of application No. 09/795,794, filed on Feb. 28, 2001, which is a continuation-in-part of application No. 09/516,753, filed on Mar. 1, 2000.
(60) Provisional application No. 60/202,723, filed on May 8, 2000.

(51) Int. Cl.⁷ .................................................. A61F 2/06
(52) U.S. Cl. ...................................................... 623/1.15
(58) Field of Search ........................... 623/1, 1.11, 1.12, 623/1.13, 1.14, 1.15, 1.16, 1.17, 1.18, 1.19, 1.2, 1.21; 608/1.08, 191, 194, 195, 198; 600/192

(56) References Cited

U.S. PATENT DOCUMENTS 4,733,665 A 3/1988 Palmaz
4,755,593 A 7/1988 Lauren (List continued on next page.)

FOREIGN PATENT DOCUMENTS

| DE | 195 12 066 | 11/1996 | |
| DE | 19957063 | 8/2001 | ............. A61F/2/04 |
| EP | 0 830 853 | 3/1998 | |
| EP | 0 830 853 A1 | 3/1998 | ............. A61F/2/06 |
| EP | 0 970 664 A2 | 1/2000 | ............. A61F/2/06 |
| EP | 0876216 | 4/2000 | ............. B01J/35/04 |
| NZ | 280547 | 9/1998 | ............. A61F/2/06 |
| NZ | 285241 | 3/1999 | ............. A61F/2/06 |
| NZ | 331532 | 1/2000 | ............. A61F/2/06 |
| WO | WO 96/26689 | 9/1996 | ............. A61F/2/06 |
| WO | WO 97/07889 | 3/1997 | ............. B01J/35/04 |

(List continued on next page.)

OTHER PUBLICATIONS

Singapore Examination Report.
New Zealand Examination Report (May 24, 2001) & (Mar. 6, 2001).
German Office Action (1 page, File # 10109508.2–43).
Cancellation Proceeding against DE Patent No. 20108764.
Cancellation Proceeding against DE Patent No. 20108765.
Two European Search Reports.
PCT Search Reports.

*Primary Examiner*—Vy Q. Bui
(74) *Attorney, Agent, or Firm*—Morgan & Finnegan, LLP

(57) ABSTRACT

An intravascular stent especially suited for implanting in curved arterial portions. The stent retains longitudinal flexibility after expansion. The stent includes a plurality of first circumferential bands containing a pattern of loops at a first frequency and a plurality of second circumferential bands containing a pattern of loops at a second frequency higher than said first frequency, alternating with said first circumferential bands and periodically coupled thereto to form cells. The high frequency elements provide a flexibility after expansions which can be repeatedly stress by the beating heart, with out exceeding the elastic limit of the stent material.

22 Claims, 7 Drawing Sheets

U.S. PATENT DOCUMENTS

| | | | | |
|---|---|---|---|---|
| 4,886,062 | A | 12/1989 | Wiktor | |
| 5,037,377 | A | 8/1991 | Alonso | |
| 5,133,732 | A | 7/1992 | Wiktor | |
| 5,510,077 | A | 4/1996 | Dinh et al. | |
| 5,554,182 | A | 9/1996 | Dinh et al. | |
| 5,571,166 | A | 11/1996 | Dinh et al. | |
| 5,575,818 | A | 11/1996 | Pinchuk | |
| 5,591,224 | A | 1/1997 | Schwartz et al. | |
| 5,595,571 | A | 1/1997 | Jaffe et al. | |
| 5,628,785 | A | 5/1997 | Schwartz et al. | |
| 5,653,747 | A | 8/1997 | Dereume | |
| 5,693,085 | A | 12/1997 | Buirge et al. | |
| 5,720,777 | A | 2/1998 | Jaffe et al. | |
| 5,733,303 | A | 3/1998 | Israel et al. | |
| 5,800,507 | A | 9/1998 | Schwartz | |
| 5,800,508 | A | 9/1998 | Goicoechea et al. | 623/1 |
| 5,807,404 | A | 9/1998 | Richter | |
| 5,836,964 | A | 11/1998 | Richter et al. | |
| 5,843,180 | A | 12/1998 | Jaffe et al. | 623/2 |
| 5,843,181 | A | 12/1998 | Jaffe et al. | |
| 5,849,034 | A | 12/1998 | Schwartz | |
| 5,855,597 | A | 1/1999 | Jayaraman | 623/1 |
| 5,855,600 | A | 1/1999 | Alt | |
| 5,865,723 | A | 2/1999 | Love | |
| 5,895,407 | A | 4/1999 | Jayaraman | |
| 5,922,021 | A | 7/1999 | Jang | 623/1 |
| 5,997,973 | A | 12/1999 | Bianca, Jr. | |
| 6,013,091 | A | 1/2000 | Ley et al. | 606/191 |
| 6,017,365 | A | 1/2000 | Von Oepen | |
| 6,053,941 | A | 4/2000 | Lindenberg et al. | |
| 6,120,847 | A | 9/2000 | Yang et al. | 427/335 |
| 6,132,461 | A | 10/2000 | Thompson | 623/1.15 |
| 6,159,237 | A | 12/2000 | Alt et al. | 623/1.11 |
| 6,162,245 | A | * 12/2000 | Jayaraman | 623/1.15 |
| 6,179,868 | B1 | 1/2001 | Burpee et al. | 623/1.17 |
| 6,193,747 | B1 | 2/2001 | Von Oepen | 623/1.15 |
| 6,221,098 | B1 | 4/2001 | Wilson et al. | 623/1.11 |
| 6,231,598 | B1 | * 5/2001 | Berry et al. | 623/1.15 |
| 6,241,762 | B1 | 6/2001 | Shanley | |
| 6,251,134 | B1 | 6/2001 | Alt et al. | 623/1.16 |
| 6,299,604 | B1 | 10/2001 | Ragheb et al. | 604/265 |
| 6,348,065 | B1 | 2/2002 | Brown et al. | 623/1.16 |
| 6,383,213 | B2 | 5/2002 | Wilson et al. | 623/1.15 |
| 6,387,120 | B2 | 5/2002 | Wilson et al. | 623/1.11 |
| 6,409,753 | B1 | 6/2002 | Brown et al. | 623/1.15 |
| 6,416,538 | B1 | 7/2002 | Ley et al. | 623/1.15 |
| 6,428,569 | B1 | 8/2002 | Brown | 623/1.15 |
| 6,478,815 | B1 | 11/2002 | Alt | 623/1.115 |
| 2001/0056298 | A1 | 12/2001 | Brown et al. | 623/1.16 |
| 2002/0007212 | A1 | 1/2002 | Brown et al. | 623/1.16 |
| 2002/0055770 | A1 | 5/2002 | Doran et al. | 623/1.15 |
| 2002/0103529 | A1 | 8/2002 | Pinchasik et al. | 623/1.15 |
| 2002/0116049 | A1 | 8/2002 | Girton et al. | 623/1.15 |
| 2002/0138136 | A1 | 9/2002 | Chandresekaran et al. | 623/1.34 |
| 2002/0177893 | A1 | 11/2002 | Brown et al. | 623/1.16 |

FOREIGN PATENT DOCUMENTS

| | | | |
|---|---|---|---|
| WO | WO 97/32544 | 9/1997 | A61F/2/06 |
| WO | WO 98 35634 | 8/1998 | |
| WO | WO 98/35634 | 8/1998 | A61F/2/06 |
| WO | 99/39660 | 8/1999 | A61F/2/06 |
| WO | WO 99/44543 | 9/1999 | A61F/2/06 |
| WO | 99/62431 | 12/1999 | A61F/2/06 |
| WO | WO 00/30563 | 6/2000 | A61F/2/06 |

* cited by examiner

LONGITUDINALLY FLEXIBLE STENT

RELATED APPLICATIONS

This application is a continuation-in-part of Ser. No. 09/795,794 filed Feb. 28, 2001, which is a continuation-in-part of Ser. No. 09/516,753 filed Mar. 1, 2000 and which also claims the priority of Provisional Application No. 60/202,723, filed May 8, 2000.

FIELD OF THE INVENTION

The present invention relates generally to stents, which are endoprostheses implanted into vessels within the body, such as blood vessels, to support and hold open the vessels, or to secure and support other endoprostheses in the vessels. In particular, the present invention relates to a stent which is longitudinally flexible before and after expansion.

BACKGROUND OF THE INVENTION

Various stents are known in the art. Typically stents are generally tubular in shape, and are expandable from a relatively small, unexpanded diameter to a larger, expanded diameter. For implantation, the stent is typically mounted on the end of a catheter, with the stent being held on the catheter at its relatively small, unexpanded diameter. By the catheter, the unexpanded stent is directed through the lumen to the intended implantation site. Once the stent is at the intended implantation site, it is expanded, typically either by an internal force, for example by inflating a balloon on the inside of the stent, or by allowing the stent to self-expand, for example by removing a sleeve from around a self-expanding stent, allowing the stent to expand outwardly. In either case, the expanded stent resists the tendency of the vessel to narrow, thereby maintaining the vessel's patency.

U.S. Pat. No. 5,733,303 to Israel et al. ("'303"), which is expressly incorporated by reference, shows a unique stent formed of a tube having a patterned shape which has first and second meander patterns having axes extending in first and second directions. The second meander patterns are intertwined with the first meander patterns to form flexible cells. Stents such as this one are very flexible in their unexpanded state such that they can be tracked easily down tortuous lumens. Upon expansion, these stents provide excellent radial support, stability, and coverage of the vessel wall. These stents are also conformable, in that they adapt to the shape of the vessel wall during implantation.

One feature of stents with a cellular mesh design such as this one, however, is that they have limited longitudinal flexibility after expansion, which may be a disadvantage in particular applications. This limited longitudinal flexibility may cause stress points at the end of the stent and along the length of the stent. Conventional mesh stents like that shown in U.S. Pat. No. 4,733,665 may simply lack longitudinal flexibility, which is illustrated by FIG. 1, a schematic diagram of a conventional stent 202 in a curved vessel 204.

To implant a stent, it maybe delivered to a desired site by a balloon catheter when the stent is in an unexpanded state. The balloon catheter is then inflated to expand the stent, affixing the stent into place. Due to the high inflation pressures of the balloon—up to 20 atm—the balloon causes the curved vessel 204 and even a longitudinally flexible stent to straighten when it is inflated. If the stent, because of the configuration of its mesh is or becomes relatively rigid after expansion, then the stent remains or tends to remain in the same or substantially the same shape after deflation of the balloon. However, the artery attempts to return to its natural curve (indicated by dashed lines) in FIG. 1 with reference to a conventional mesh stent. The mismatch between the natural curve of the artery and the straightened section of the artery with a stent may cause points of stress concentration 206 at the ends of the stent and stress along the entire stent length. The coronary vasculature can impose additional stress on stents because the coronary vasculature moves relatively significant amounts with each heartbeat. For illustration purposes, the difference between the curve of the vessel and the straightened stent has been exaggerated in FIG. 1.

U.S. Pat. No. 5,807,404 to Richter, which is expressly incorporated by reference, shows another stent which is especially suited for implantation into curved arterial portions or osteal regions. This stent can include sections adjacent the end of the stent with greater bending flexibility than the remaining axial length of the stent. While this modification at the end of the stent alleviates the stress at the end points, it does not eliminate the stress along the entire length of the stent.

Various stents are known that retain longitudinal flexibility after expansion. For example, U.S. Pat. Nos. 4,886,062 and 5,133,732 to Wiktor ("the Wiktor '062 and '732 patents") show various stents formed of wire wherein the wire is initially formed into a band of zig-zags forming a serpentine pattern, and then the zig-zag band is coiled into a helical stent. The stents are expanded by an internal force, for example by inflating a balloon.

The coiled zig-zag stents that are illustrated in FIGS. 1 through 6 of the Wiktor '062 and '732 patents are longitudinally flexible both in the expanded and unexpanded condition such that they can be tracked easily down tortuous lumens and such that they conform relatively closely to the compliance of the vessel after deployment. While these stents are flexible, they also have relatively unstable support after expansion. Furthermore, these stents leave large portions of the vessel wall uncovered, allowing tissue and plaque prolapse into the lumen of the vessel.

Thus, it is desired to have a stent which exhibits longitudinal flexibility before expansion such that it can easily be tracked down tortuous lumens and longitudinal flexibility after expansion such that it can comply with the vessel's natural flexibility and curvature while still providing continuous, stable coverage of a vessel wall that will minimize tissue sag into the lumen.

SUMMARY OF THE INVENTION

Embodiments of the present invention provide a stent that is longitudinally flexible before expansion so that it can easily be tracked down tortuous vessels and remains longitudinally flexible after expansion such that it will substantially eliminate any stress points by complying with the vessel's flexibility and assuming the natural curve of the vessel.

Embodiments of the present invention also to provide a stent that is longitudinally flexible after delivery such that it flexes during the cycles of the heartbeat to reduce cyclic stress at the ends of the stent and along the stent. In some embodiments, the stress experienced during such flexes is below the elastic limit of the material and thus, a very high number of flexes, without fatigue is possible In addition, embodiments of the present invention provide a stent with a closed cell pattern such that it provides good coverage and support to a vessel wall after expansion.

A stent according to the invention retains the longitudinal flexibility associated with the '303 cellular stent in its unexpanded state, and has increased longitudinal flexibility in the expanded state. The stent does so without sacrificing scaffolding—i.e. coverage of the vessel wall—or radial support.

DETAILED DESCRIPTION OF THE INVENTION

Figure 1:
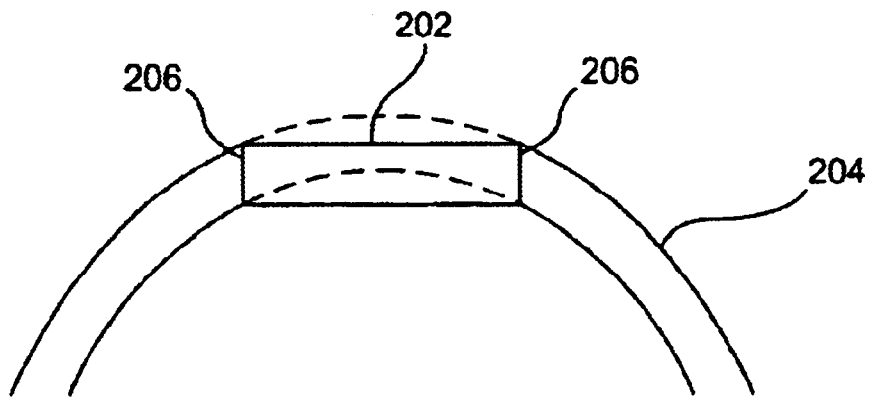
FIG. 1 shows a schematic diagram of a conventional rigid stent deployed in a curved lumen.
Figure 2:
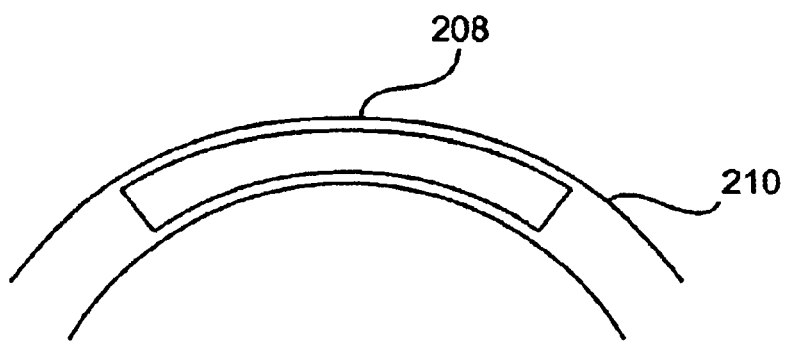
FIG. 2 shows a schematic diagram of a stent of the present invention deployed in a curved lumen.

FIG. 2 shows a schematic diagram of a longitudinally flexible stent 208 of the present invention. The stent 208 may be delivered to a curved vessel 210 by a balloon catheter, and implanted in the artery by inflating the balloon. As described before, the balloon causes the artery to straighten upon inflation of the balloon. However, upon deflation of the balloon, the stent 208 assumes the natural curve of the vessel 210 because it is and remains longitudinally flexible after expansion. This reduces any potential stress points at the ends of the stent and along the length of the stent. Furthermore, because the stent is longitudinally flexible after expansion, the stent will flex longitudinally with the vessel during the cycles caused by a heartbeat. This also reduces any cyclic stress at the ends of the stent and along the length of the stent.

Figure 3:
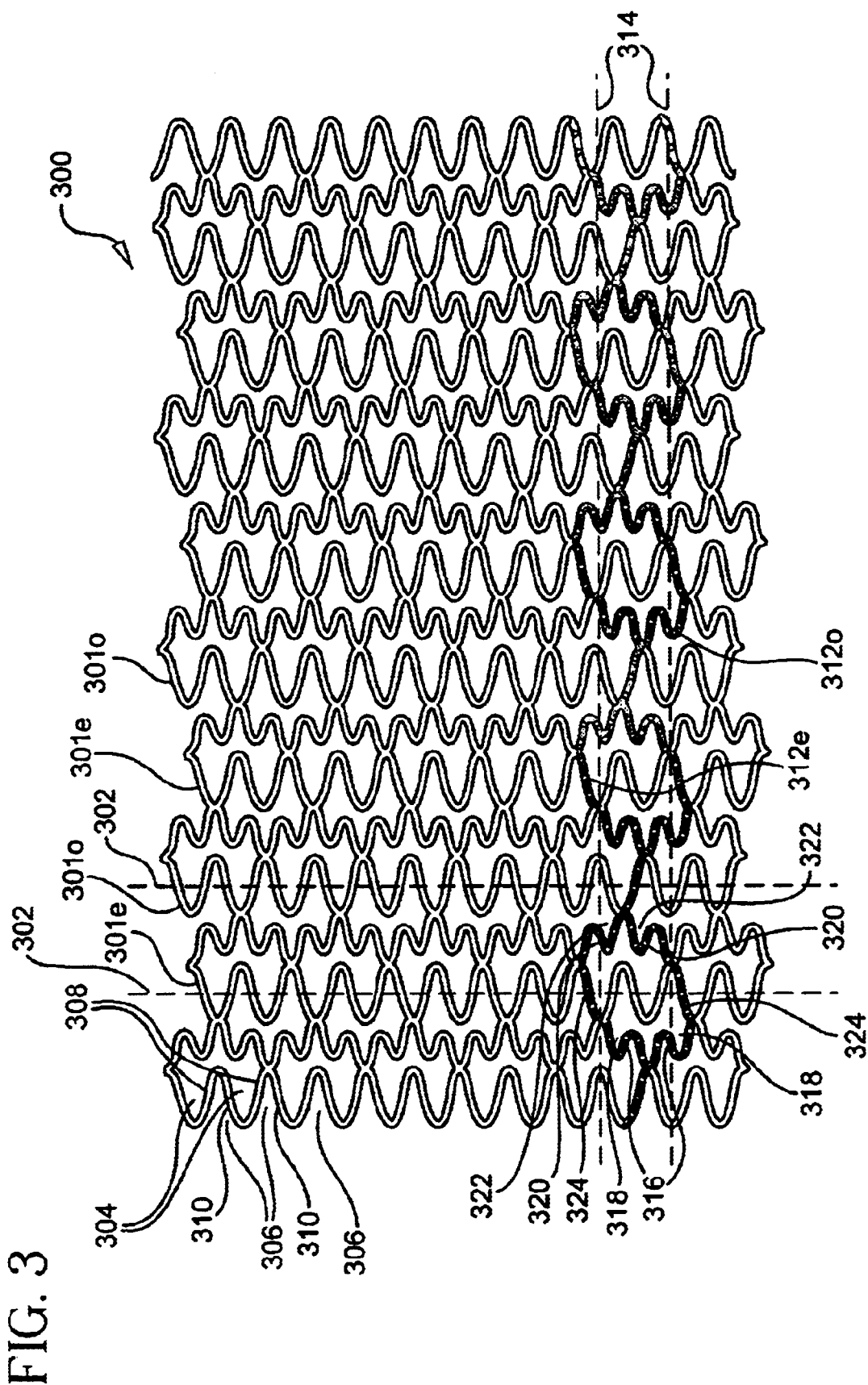
FIG. 3 shows a pattern for a stent made in accordance with the present invention.

FIG. 3 shows a pattern of a stent according to the present invention. This pattern may be constructed of known materials, and for example stainless steel, but it is particularly suitable to be constructed from NiTi. The pattern can be formed by etching a flat sheet of NiTi into the pattern shown. The flat sheet is formed into a stent by rolling the etched sheet into a tubular shape, and welding the edges of the sheet together to form a tubular stent. The details of this method of forming the stent, which has certain advantages, are disclosed in U.S. Pat. Nos. 5,836,964 and 5,997,973, which are hereby expressly incorporated by reference. Other methods known to those of skill in the art such as laser cutting a tube or etching a tube may also be used to construct a stent which uses the present invention. After formation into a tubular shape, a NiTi stent is heat treated, as known by those skilled in the art, to take advantage of the shape memory characteristics of NiTi and its superelasticity.

The pattern 300 is formed from a plurality of each of two orthogonal meander patterns which patterns are intertwined with each other. The term "meander pattern" is taken herein to describe a periodic pattern about a center line and "orthogonal meander patterns" are patterns whose center lines are orthogonal to each other.

A meander pattern 301 is a vertical sinusoid having a vertical center line 302. It will be recognized that this is not a perfect sinusoid, but only an approximation thereof. Thus, as used herein, the term sinusoid refers to a periodic pattern which varies positively and negatively symmetrically about an axis; it need not be an exact sine function. A meander pattern 301 has two loops 304 and 306 per period wherein loops 304 open to the right while loops 306 open to the left. Loops 304 and 306 share common members 308 and 310, where member 308 joins one loop 304 to its following loop 306 and member 308 joins one loop 306 to its following loop 304. The vertical sinusoid of meander pattern 301 has a first frequency.

A meander pattern 312 (two of which have been shaded for reference) is a horizontal pattern having a horizontal center line 314. A horizontal meander pattern 312 also has loops labeled 316, 318, 320, 322, and between the loops of a period is a section labeled 324. Looked at another way, these loops are part of a vertical sinusoid 303 which has a higher frequency than that of the meander patterns 301. Vertical sinusoids 301 alternate with vertical sinusoids 303. Vertical sinusoids 303 have a second frequency higher than the first frequency of the vertical meander patterns, i.e., sinusoids 301.

Vertical meander pattern 301 is provided in odd and even (o and e) versions which are 180N out of phase with each other. Thus, each left opening loop 306 of meander pattern 301o faces a right opening loop 304 of meander pattern 301e and a right opening loop 304 of meander pattern 301o faces a left opening loop 306 of meander pattern 301e.

The horizontal meander pattern 312 is also provided in odd and even forms. The straight sections 324 of the horizontal meander pattern 312e intersect with every third common member 310 of the even vertical meander pattern 301e. The straight sections 324 of the horizontal meander pattern 312o also intersect with every third common member 310 of the odd vertical meander pattern 301. Viewed as vertical sinusoids 303, alternating sinusoids 303 are intermittently coupled to the meander patterns 301. For example, between points 315 and 317, where vertical pattern 303 is coupled to vertical pattern 301e, there are two loops 306 and one loop 304 of vertical pattern 301e and three loops 319 and two loops 321 of vertical pattern 303. This corresponds to two cycles of pattern 301e and 3 cycles of pattern 303. Similarly, between two points of coupling between vertical pattern 301o and vertical pattern 303 are two loops 304 and one loop 306, again making two cycles. There will be three loops 321 and two loops 319, again equal to three cycles of pattern 303.

Upon expansion of the stent, the loops of the vertical meander patterns 301 open up in the vertical direction. This causes them to shorten in the horizontal direction. The loops in the horizontal meander pattern 312 open up both in the vertical direction and the horizontal direction, compensating for the shortening of the loops of the vertical meander patterns.

Figure 7:
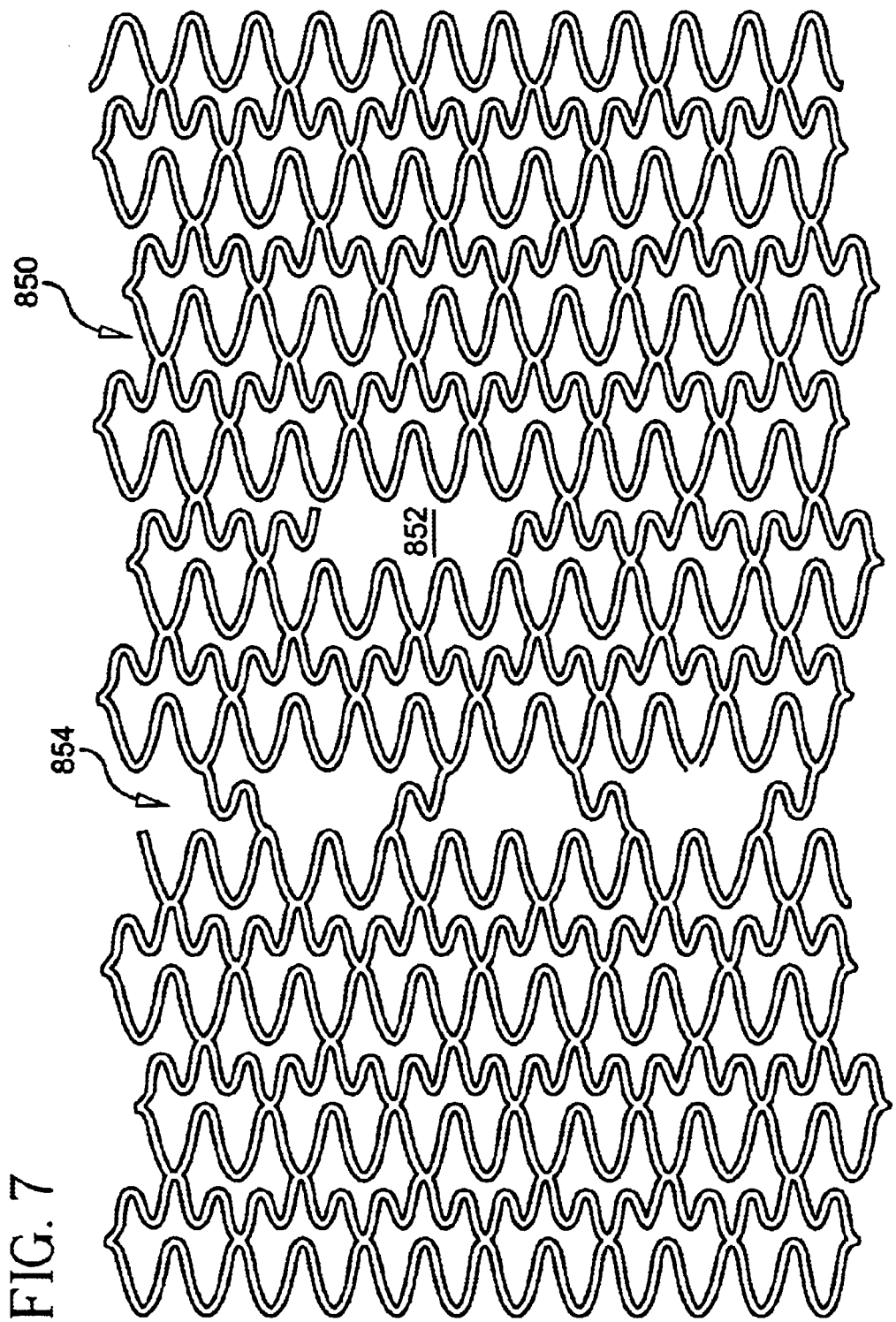
FIG. 7 shows a pattern for a stent constructed according to the principles of the invention which has variable geometry along its length.
Figure 8A:
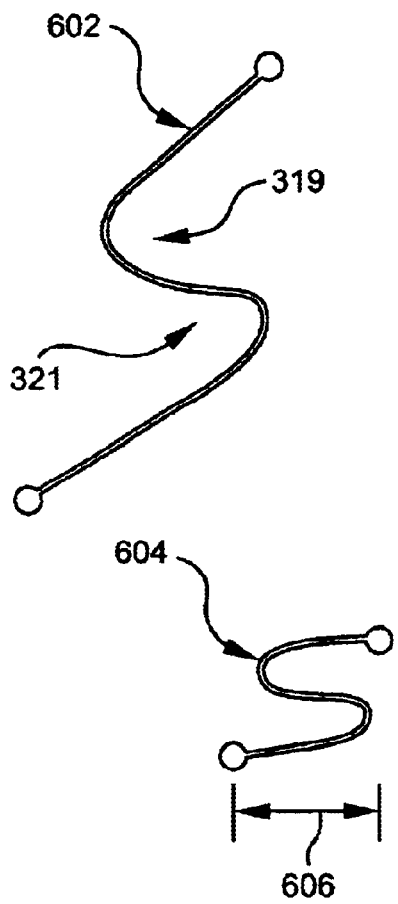
FIG. 8A shows the expansion of a portion of a horizontal meander pattern built according to the principles of the invention.
Figure 8B:
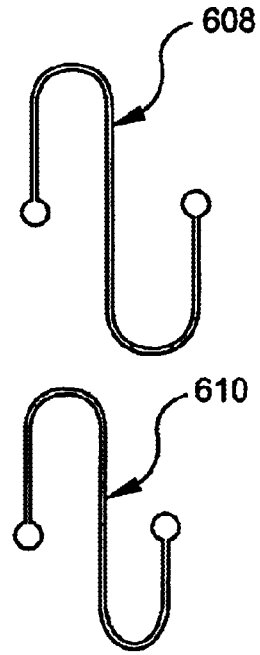
FIG. 8B shows the expansion of a portion of another horizontal meander pattern.

It should be noted that the loops of the horizontal meander pattern 312, which are the loops of the vertical pattern 303 in the present invention avoids foreshortening in a self-expanding stent in a particularly effective manner. A self-expanding stent formed of a shape-memory alloy must be compressed from an expanded position to a compressed position for delivery. As shown in FIG. 7, because of the configuration of the loops 319 and 321 of the horizontal meander pattern 312, when the stent is compressed from an expanded position 602 to a compressed position 604, the length 606 of the horizontal meander pattern (width of the vertical pattern 330) naturally shrinks. Consequently, when the stent expands, the loops 319 and 321 elongate and compensate for the shortening of the vertical meander patterns 301e and 301o as the vertical meander patterns 301e and 301o expand. In contrast, a horizontal meander pattern with such shapes as N-shapes will not naturally shrink longitudinally when compressed from an expanded position 608 to a compressed position 610, as illustrated in FIG. 8.

A stent formed from the pattern of FIG. 3 and made of NiTi is particularly well suited for use in the carotid artery or other lumens subject to an outside pressure. One reason is that because the stent is formed of NiTi, it is reboundable, which is a desirable property for stents placed in the carotid artery. The other reason is that the stent of FIG. 3 offers excellent scaffolding, which is particularly important in the carotid artery. Scaffolding is especially important in the carotid artery because dislodged particles in the artery may embolize and cause a stroke.

Figure 4:
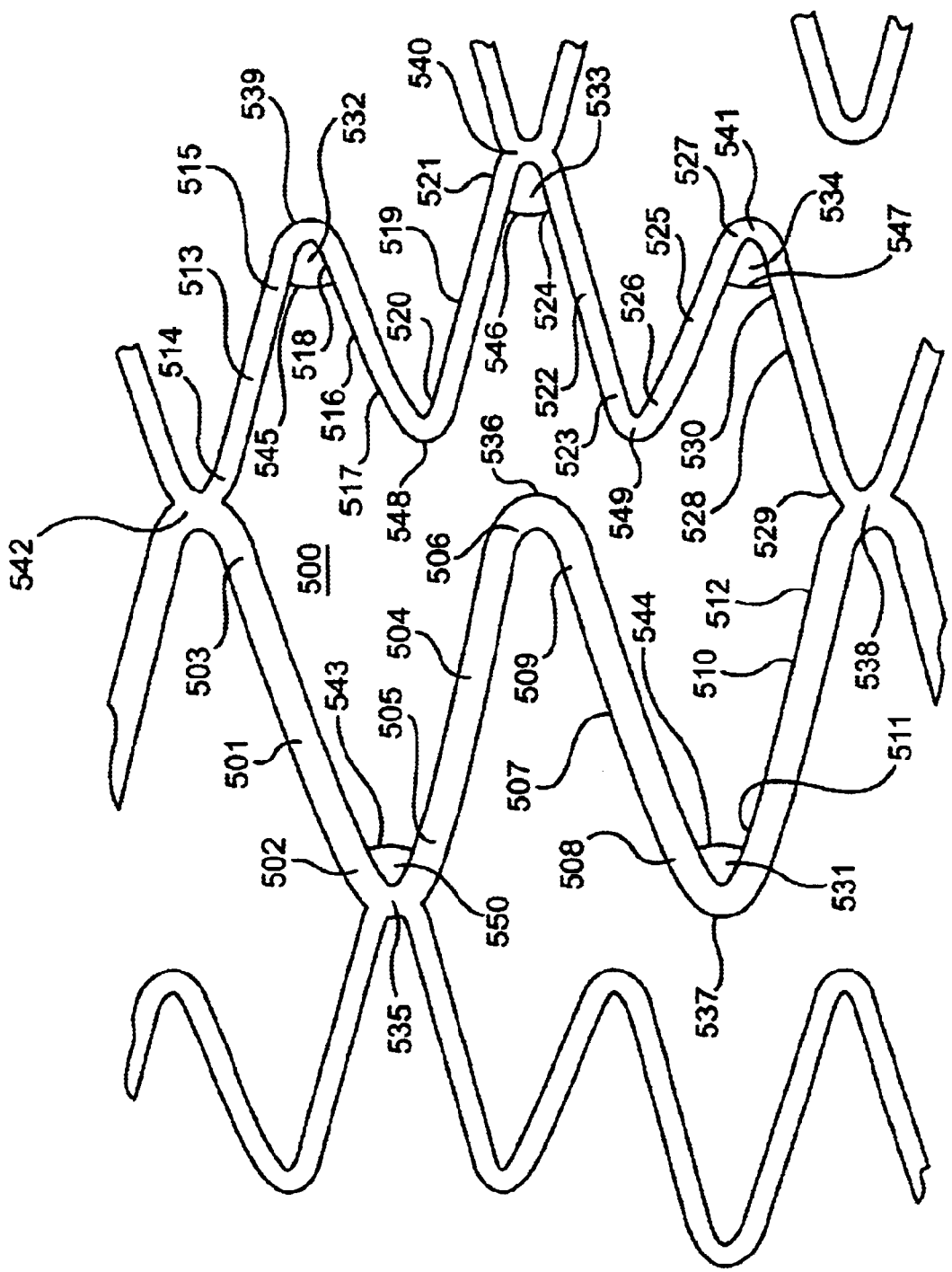
FIG. 4 shows an enlarged view of one cell of the pattern of FIG. 3.

FIG. 4 is an expanded view of one flexible cell 500 of the pattern of FIG. 3. Each flexible cell 500 includes: a first member 501 having a first end 502 and a second end 503; a second member 504 having a first end 505 and a second end 506; a third member 507 having a first end 508 and a second end 509; and a fourth member 510 having a first end 511 and a second end 512. The first end 502 of the first member 501 is joined to the first end 505 of the second member 504 by a first curved member 535 to form a first loop 550, the second end 506 of the second member 504 is joined to the second end 509 of the third member 508 by a second curved member 536, and the first end 508 of the third member 507 is joined to the first end 511 of the fourth member 510 by a third curved member 537 to form a second loop 531. The first loop 530 defines a first angle 543. The second loop 531 defines a second angle 544. Each cell 500 also includes a fifth member 513 having a first end 514 and a second end 515; a sixth member 516 having a first end 517 and a second end 518; a seventh member 519 having a first end 520 and a second end 521; an eighth member 522 having a first end 523 and a second end 524; a ninth member 525 having a first end 526 and a second end 527; and a tenth member having a first end 529 and a second end 530. The first end 514 of the fifth member 513 is joined to the second end 503 of the first member 501 at second junction point 542, the second end 515 of the fifth member 513 is joined to the second end 518 of the sixth member by a curved member 539 to form a third loop 532, the first end 517 of the sixth member 516 is joined to the first end 520 of the seventh member 519 by a fifth curved member 548, the second end 521 of the seventh member 519 is joined to the second end 524 of the eighth member 522 at third junction point 540 to form a fourth loop 533, the first end 523 of the eighth member 522 is joined to the first end 526 of the ninth member 525 by a sixth curved member 549, the second end 526 of the ninth member 525 is joined to the second end 530 of the tenth member 528 by a seventh curved member 541 to form a fifth loop 534, and the first end 529 of the tenth member 528 is joined to the second end 512 of the fourth member 510. The third loop 532 defines a third angle 545. The fourth loop 533 defines a fourth angle 546. The fifth loop 534 defines a fifth angle 547.

In the embodiment shown in FIG. 4, the first member 501, the third member 507, the sixth member 516, the eighth member 522, and the tenth member 528 have substantially the same angular orientation to the longitudinal axis of the stent and the second member 504, the fourth member 510, the fifth member 513, the seventh member 519, and the ninth member 512 have substantially the same angular orientation to the longitudinal axis of the stent. In the embodiment shown in FIG. 4, the lengths of the first, second, third and fourth members 501, 504, 507, 510 are substantially equal. The lengths of the fifth, sixth, seventh, eighth, ninth and tenth members 513, 516, 519, 522, 525, 528 are also substantially equal. Other embodiments where lengths of individual members are tailored for specific applications, materials of construction or methods of delivery are also possible, and may be preferable for them. It can be seen that each cell includes two cycles of the lower frequency vertical pattern and three cycles of the higher frequency vertical pattern. The first, second, third, and fourth members 501, 504, 507, 510 may have a width that is greater than the width of the fifth, sixth, seventh, eighth, ninth, and tenth members 513, 516, 519, 522, 525, 528 in that cell. The differing widths of the first, second, third, and fourth members and the fifth, sixth, seventh, eighth, ninth, and tenth members with respect to each other contribute to the overall flexibility and resistance to radial compression of the cell. The widths of the various members can be tailored for specific applications. For example, the ratio of width may be approximately 50 70%. The fifth, sixth, seventh, eighth, ninth, and tenth members may be optimized predominantly to enable longitudinal flexibility, both before and after expansion, while the first, second, third, and fourth members may be optimized predominantly to enable sufficient resistance to radial compression to hold a vessel open. Although specific members may be optimized to predominantly enable a desired characteristic, all the portions of the cell interactively cooperate and contribute to the characteristics of the stent.

Figure 5:
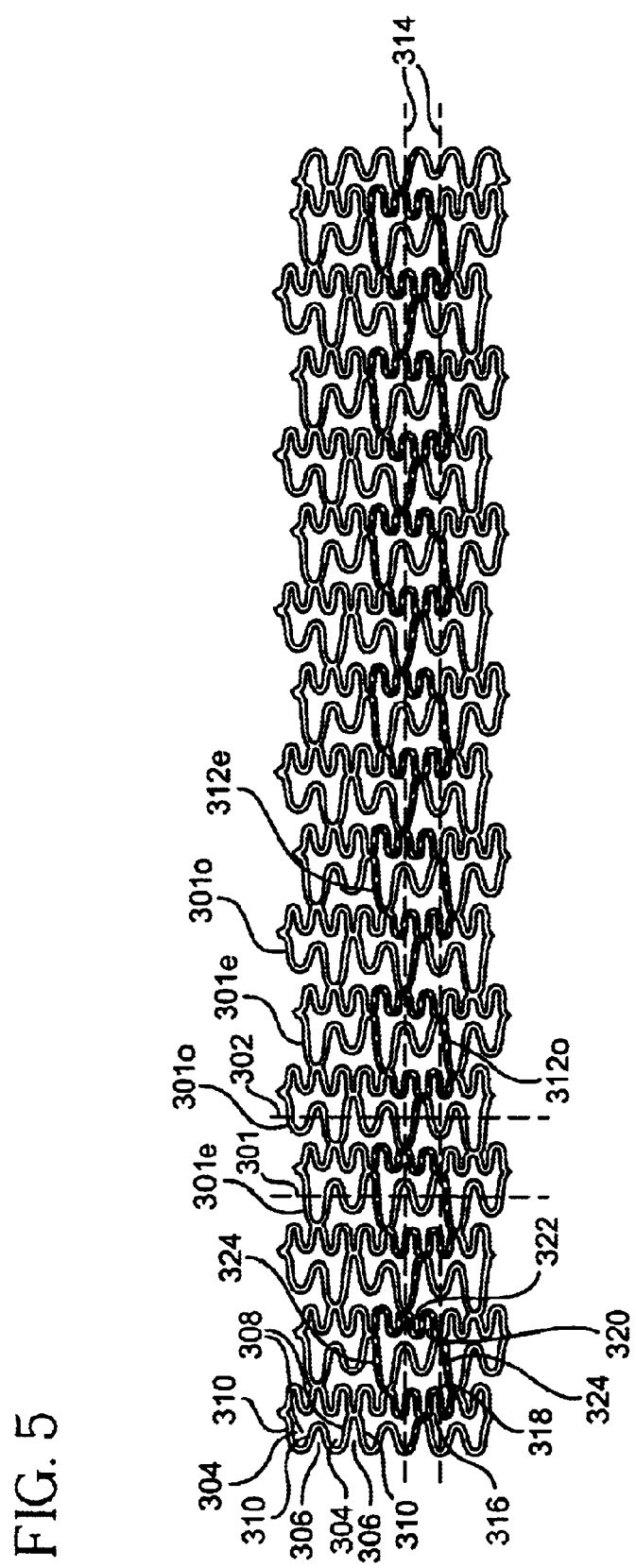
FIG. 5 shows a pattern for a stent made in accordance with the present invention.
Figure 6:
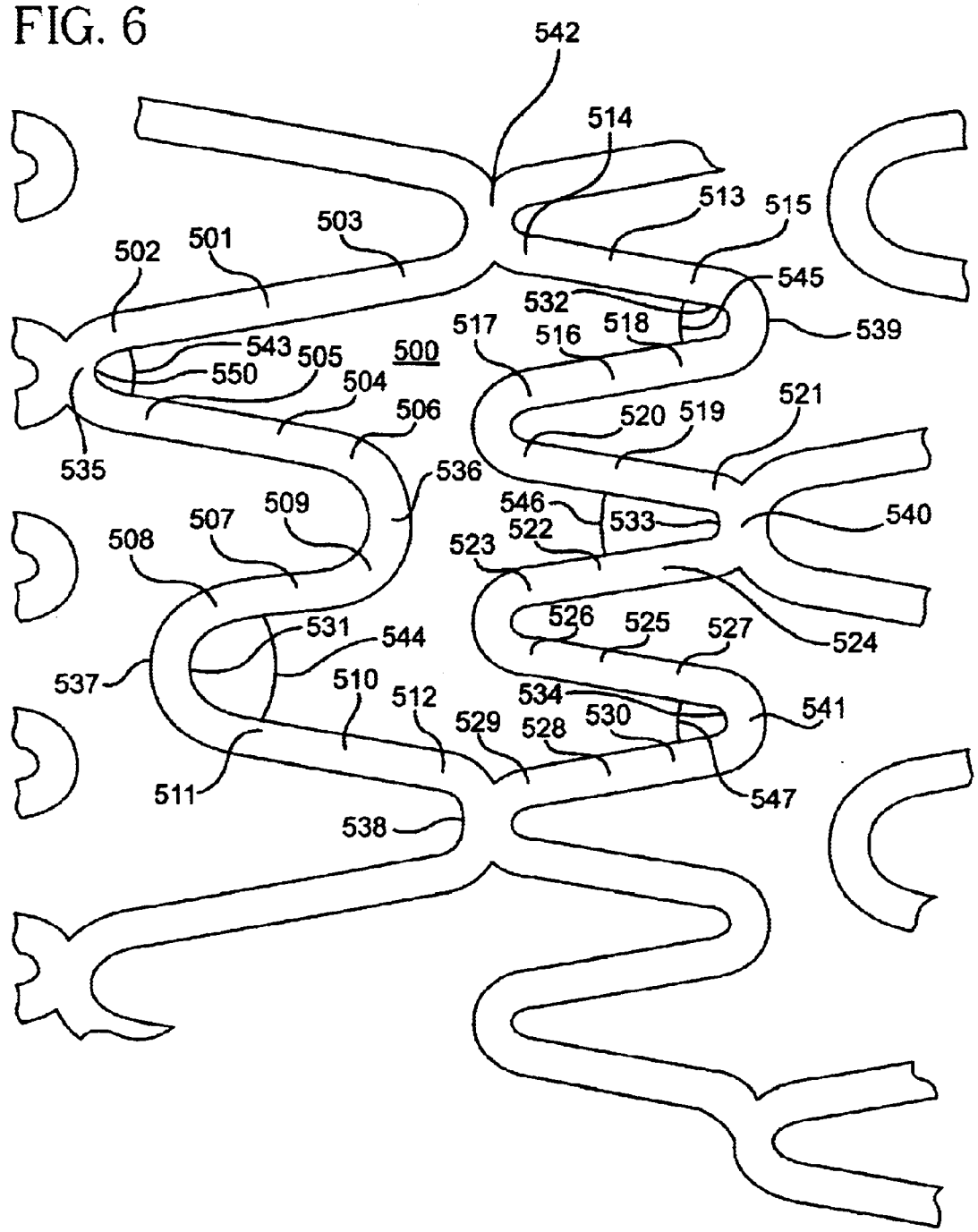
FIG. 6 shows an enlarged view of one cell of the pattern of FIG. 5.

FIGS. 5 and 6 show a pattern and an expanded view of one cell of an embodiment of the present invention which is specially adapted for a stent made of stainless steel. The pattern is similar to the pattern of FIGS. 3 and 4, and the same reference numerals are used to indicate the generally corresponding parts.

The embodiments of FIGS. 3 and 5 can also be viewed as being made up of high frequency and low frequency vertical sinusoidal patterns or vertical loop containing sections which are arranged generally in the circumferential direction and which are periodically interconnected. Thus, there is a first loop containing section with loops occurring at a first frequency extending along line 301 and a second loop containing section with also occurring at said first frequency extending along line 302. A third loop containing section 303 extending along line 305 has loops occurring at a second frequency that is higher than said first frequency. It is disposed between the first and second loop containing sections and alternately joined to the first and second loop containing sections. In the illustrated embodiment, the high frequency is in a ratio of 3/2 to the low frequency. As noted above, the higher frequency loop containing elements are smaller in width. The relative widths can be selected so that the high frequency elements are crimpable to the same diameter as the lower frequency elements. The higher frequency elements provide improved flexibility.

Furthermore the high frequency vertical patterns of smaller width result in elements having a lower maximal strain. Specifically, when the stent is expanded, the lower maximal strain is below the maximum strain without nonelastic deformation for the material of the stent. In this embodiment where the stent is made of stainless steel the lower maximal strain is below approximately 0.5%, even for a 150 B bend, as confirmed by finite element analysis. On the other hand, in a '303 type stent, for an equivalent amount of bending, exhibits a maximum strain of 8%. Thus, the increased flexibility of the stent of the present invention means that, in addition to conforming better to the curved lumen, it will bend with each beat of the heart. The strain during heartbeat happens 8,000,000 times every year and cannot be much above elastic limit without the stent breaking. Since, embodiments of the present invention keep the strain below the limit means that the stent of the present invention can bend with the lumen as the heart beats, for many years without breaking.

Also in this embodiment of the invention, for example, the second loops 531 are made stronger by shortening the third and fourth members 507, 510. This helps assure that the second loops do not "flare out" during delivery of the stent through tortuous anatomy. This "flaring out" is not a concern with NiTi stents which are covered by a sheath during delivery.

Furthermore, the length of the members in this embodiment may be shorter than the length of the corresponding members in the embodiment illustrated in FIGS. 3 and 4. Typically, the amount of strain allowed in a self-expanding NiTi stent may be around 10%. In a stainless steel stent, the amount of strain allowed during the plastic deformation which take place, for example, during expansion, typically may be 20% or greater. Therefore, to facilitate stents made of NiTi and stents made of stainless steel expanding to comparable diameters, the members of the NiTi stent may be longer than the members of a stainless steel stent.

In the particular embodiments described above, the stent is substantially uniform over its entire length. However, other applications where portions of the stent are adapted to provide different characteristics are also possible. For example, as shown in FIG. 7, a band of cells 850 may be designed to provide different flexibility characteristics or different radial compression characteristics than the remaining bands of cells by altering the widths and lengths of the members making up that band. Or, the stent may be adapted to provide increased access to a side branch lumen by providing at least one cell 852 which is larger in size then the remaining cells, or by providing an entire band of cells 854 which are larger in size than the other bands of cells. Note that the cells 854 are formed by a first loop containing section 856, which arranged generally in the circumferential direction, with the loops in first loop containing section 856 occurring at a first frequency; a second loop containing section 858, which is also arranged generally in the circumferential direction, with the loops in the second loop containing section 858 also occurring at the first frequency; and third loop containing sections 860, which are arranged generally in the circumferential direction. The loops in said third loop containing sections 860 occur at a second frequency that is higher than said first frequency and are disposed between and first and second loop containing sections and alternately joined to said first and second loop containing sections.

Or, the stent may be designed to expand to different diameters along the length of the stent. The stent may also be treated after formation of the stent by coating the stent with a medicine, plating the stent with a protective material, plating the stent with a radiopaque material, or covering the stent with a material.

Thus, what is described is a longitudinally flexible stent that utilizes a closed cell structure to provide excellent coverage of the vessel wall. The general concepts described herein can be utilized to form stents with different configurations than the particular embodiments described herein. For example, the general concepts can be used to form bifurcated stents. It will be appreciated by persons skilled in the art that the present invention is not limited to what has been particularly shown and described above. Rather, the scope of the present invention is defined by the claims which follow.

What is claimed is:

1. A stent comprising
    a first loop containing section, the first loop containing section arranged generally in the circumferential direction, the loops in said first loop containing section occurring at a first frequency;
    a second loop containing section, the second loop containing section arranged generally in the circumferential direction the loops in said second loop containing section also occurring at said first frequency and
    a third loop containing section, the loops in said third loop containing section occurring at a second frequency that is higher than said first frequency, the third loop containing section disposed in the generally circumferential space between said first and second loop containing sections and alternately joined to said first and second loop containing sections such that said first and second loop containing sections are joined together through the third loop containing section without connection directly between the first and second loop containing sections, wherein the first and second loop containing sections have two cycles for every three cycles of said third loop containing section, wherein the first loop containing section or the second loop containing section and the third loop containing section form at least one cell, the first loop containing section or the second loop containing section in the at least one cell further has at least one loop longitudinally shorter than another loop in the first loop containing section or the second loop containing section.

2. A stent according to claim 1, wherein the first loop and second loop containing sections are relatively adapted to enable radial support and the third loop containing section is relatively adapted to enable longitudinal flexibility.

3. A stent according to claim 1, wherein the first loop and second loop containing sections have wider struts than the third loop containing section.

4. A stent according to claim 1, wherein the relative widths of said first, second, and third loop containing sections are such that when said stent is crimped for insertion into a lumen of a blood vessel, said third loop containing section is crimpable to essentially the same diameter as said first loop and second loop containing sections.

5. A stent according to any of claim 1, wherein the second frequency elements provide improved flexibility.

6. A stent according to claim 5, wherein, while flexing, the second frequency elements have maximal strain that is lower than the elastic limit for the material of the stent.

7. A stent according to claim 6, wherein, the maximal strain of the expanded stent within a blood vessel caused by repeated flexing is below the strain which would cause permanent deformation for the material of the stent.

8. A stent according to claim 7, wherein, said stent is made of stainless steel and said maximal strain is below approximately 0.5%.

9. A stent according to any of claim 8, wherein the first and second loop containing sections are 180 degrees out of phase with each other.

10. A stent according to claim 1, wherein substantially each cell in the stent encompasses the same area.

11. A stent according to claim 1, wherein at least one cell is arranged so that when expanded a length of the cell along a circumference of the stent is longer than a length of a cell along the longitudinal axis of the stent.

12. A stent according to claim 1, wherein at least one cell of the stent is symmetrical about a line parallel to a longitudinal axis of the stent.

13. A stent comprising:
 a plurality of first circumferential bands containing a pattern of loops at a first frequency,
 a plurality of second circumferential bands containing a pattern of loops at a second frequency higher than said first frequency, alternating with said first circumferential bands and periodically coupled thereto to form cells such that said first circumferential bands are joined together through said second circumferential bands without connection directly between said first circumferential bands
 wherein the first circumferential bands containing a pattern of loops are comprised of even first circumferential bands containing a pattern of loops and odd first circumferential bands containing a pattern of loops which are 180 degrees out of phase with the loops of the even first circumferential bands, an odd first circumferential band occurring between every two even first circumferential bands, wherein each cell includes two cycles of one of said plurality of first circumferential bands and three cycles of one of said plurality of second circumferential bands such that the first circumferential band has at least one loop shorter than another loop in the first circumferential band.

14. A stent according to claim 13, wherein each cell includes a number of loops of said first circumferential band corresponding to two cycles of said first frequency and a number of loops of said second circumferential band corresponding to three cycles of said second frequency.

15. A stent according to claim 13, wherein the first circumferential bands have struts that are wider than the struts in said second circumferential bands.

16. A stent according to claim 15, wherein the relative widths of said loops is such that when said stent is crimped for insertion into a lumen of a blood vessel, the loops of said second circumferential bands are crimpable to essentially the same diameter as the loops of said first circumferential bands.

17. A stent according to claim 15, wherein the higher frequency of the loops in said second circumferential bands provide improved flexibility.

18. A stent according to claim 17, wherein, while flexing, elements in the higher frequency loops have lower maximal strain.

19. A stent according to claim 18, wherein, the maxima strain of the expanded strain within a blood vessel cause by repeated flexing is below the maximum strain causing permanent deformation for the material of the stent.

20. A stent according to claim 18, wherein said lower maximal strain is below approximately 0.5%.

21. A stent according to claim 13, wherein the first circumferential bands have loops forming two cycles per cell.

22. A stent according to claim 13, wherein the second circumferential bands have loops forming three cycles per cell.

* * * * *

UNITED STATES PATENT AND TRADEMARK OFFICE
CERTIFICATE OF CORRECTION

PATENT NO. : 6,723,119 B2
DATED : April 20, 2004
INVENTOR(S) : Gregory Pinchasik et al.

It is certified that error appears in the above-identified patent and that said Letters Patent is hereby corrected as shown below:

Column 10,
Line 1, delete "maxima" and insert -- maximal --.
Line 2, delete "strain of the expanded strain" and insert -- strain of the expanded stent --.
Line 2, delete "cause" and insert -- caused --.

Signed and Sealed this

Twenty-first Day of June, 2005

JON W. DUDAS
*Director of the United States Patent and Trademark Office*